United States Patent [19]

Kossovsky et al.

[11] Patent Number: 4,531,934
[45] Date of Patent: Jul. 30, 1985

[54] APPARATUS FOR THE FRAGMENTATION AND ASPIRATION OF OCULAR TISSUE

[75] Inventors: Leopold V. Kossovsky; Jury K. Kravchuk, both of Gorky; Alexandr V. Boiko, Moscow; Zinovy M. Slavinsky, Gorky; Georgy E. Stolyarenko, Gorky; Irina L. Kossovskaya, Gorky; Alexandr I. Sorokin, Gorky, all of U.S.S.R.

[73] Assignee: Gorkovsky Gosudarstvenny Meditsinsky Institute Imini S.M. Kirova, Gorky, U.S.S.R.

[21] Appl. No.: 451,769

[22] Filed: Dec. 21, 1982

[51] Int. Cl.³ ............................................ A61B 17/20
[52] U.S. Cl. ........................................ 604/22; 433/91;
128/305; 604/27; 604/35
[58] Field of Search .............. 128/305, 328, 24 A, 128/66; 604/22, 27, 35; 433/91

[56] References Cited

U.S. PATENT DOCUMENTS

| | | | |
|---|---|---|---|
| 3,433,226 | 3/1969 | Boyd | 604/22 |
| 3,857,387 | 12/1974 | Shock | 128/24 A |
| 3,874,372 | 4/1975 | Le Bon | 128/66 |
| 4,178,935 | 12/1979 | Gekhman et al. | 128/328 |

Primary Examiner—C. Fred Rosenbaum
Assistant Examiner—J. L. Kruter
Attorney, Agent, or Firm—Lilling & Greenspan

[57] ABSTRACT

An apparatus for the fragmentation and aspiration of ocular tissues consists of a controlled ultrasonic generator connected to a magnetostriction converter to produce mechanical ultrasonic vibrations transmitted therefrom to a hollow needle joined thereto. The end of the needle opposing the end connected to the magnetostriction converter is adapted to be brought into contact with the ocular tissue under fragmentation and comprises an end wall portion with a through opening having a diameter substantially between ⅓ and ⅔ of the diameter of a needle bore. The surface of the needle can be fashioned into a cone or a cylinder.

5 Claims, 5 Drawing Figures

APPARATUS FOR THE FRAGMENTATION AND ASPIRATION OF OCULAR TISSUE

BACKGROUND OF THE INVENTION

1. Field of the Invention

This invention pertains to medical engineering, but more particularly to ophthalmology and provides an apparatus adapted to fragment and aspirate ocular tissues relying on the use of ultrasound. This invention will be found most useful in the operative procedures involving the removal of cataract, as well as the vitreous, blood clots, fibrin membranes, and exudates.

2. Description of the Prior Art

At the present time a highly promising technique of cataract extraction consists in fragmenting the opacified lens directly in situ combined with the simultaneous suction of the fragmented mass. This technique is far less traumatic compared to the conventional methods of cataract removal, for example, cryophakia, since it requires an operative incision of but a small size to enable the introduction of a needle or an instrument tip into the eye. A similar situation is seen in respect of excision of the pathologically affected vitreous, as well as in pathological changes involving other tissues (fibrin membranes, blood pools, exudates).

An embodiment of the method relies on the use of mechanical devices, vitreotomes, for example, such as that described in U.S. Pat. No. 3,882,872. The instrument referred to consists of a mechanical drive, aspiration unit, and a working tip shaped as two coaxially arranged tubes interacting by their cutting edges. The tissue to be removed is sucked into the passage between the tubes and is then subjected to the shearing type cutting action while the inner tube moves.

However, such mechanical devices require continuously razor-sharp cutting edges thereby restricting everyday use of the vitreotome. In this connection, ultrasound instruments such as phacoemulsifiers or fragmentors find an increasingly wide application.

U.S. Pat. No. 3,693,613 describes an apparatus for the removal of material and a method of applying high frequency vibrations. The device comprises an ultrasonic generator, magnetostriction converter, a suction means for the removal of broken tissue, and a hollow needle having a through longitudinal bore. The needle is connected to the magnetostriction converter wherefrom it receives longitudinal periodic vibrations with a frequency of about 40 KHz and an amplitude of about 30 μm. The free end portion of the needle when advanced contiguous to the lens breaks the nucleus to dust-like particles. Simultaneously, another route is used to introduce normal saline into the eyeball to dilute the broken mass and perform its aspiration via the through longitudinal bore of the needle using the suction unit provided with a pump and a motor.

A serious disadvantage of this device is the need of forcibly aspirating the broken mass by employing a special means provided with a pump. Continuous operation of the pump required throughout the extent of surgery poses the danger of abrupt pressure fluctuations within the suction system if the needle becomes blocked by large fragments broken off the lens. Such blockage of the suction channel produces surplus vacuum. Sudden dislodgement of obstruction due to changed power or frequency of the ultrasonic generator results in too much intraocular matter being sucked into the vacuum area since inertia of the feeding system delays restoration of the intraocular fluid balance. This may lead to such grave complication as ocular collapse.

The additional presence of an electric motor significantly complicates the device reducing its reliability due to a large number of moving parts and electric contact.

Moreover, the use of such a device is restricted to the removal of the lens mass, while the vitreous and other pathologically affected tissues remain inaccessible.

Another ultrasonic device designated medical machine for performing surgery and treating using the ultrasonic energy is disclosed in U.S. Pat. No. 3,990,452. The essential design of this device is similar to that mentioned above with all the inherent shortcomings thereof. However, from the above-described arrangement it is distinguished by a changed shape of the needle having a tapering neck such that its apex develops into an elongated cylindrical portion terminating by an obliquely cut end. A needle of this type allows fragmentation and aspiration of the lens mass, but its application can be extended to the vitreous and a variety of pathological tissues, for example, fibrin membranes, exudates, etc. However, such a needle is designed for a single surgery due to quick wear at the juncture of the conical and cylindrical portions.

SUMMARY

In line with the above, the principal object of the present invention is to provide an ultrasonic instrument for the fragmentation and aspiration of ocular tissues of a character dispensing with the forcible suction of broken ocular tissue by means of a special suction unit, which will substantially increase operative safety.

Another object of the present invention is to provide for a simpler design and, therefore, more reliable operation of the system reduced in bulk and more amenable to control since it does not require preliminary instruction of the attending personnel.

Still another object of the present invention is to extend the life of the needle of the apparatus providing for its repeated, over 100 times, use.

These as well as other objects are achieved by providing an apparatus adapted to fragment and remove ocular tissue comprising a controlled ultrasonic generator, a magnetostriction converter connected to an outlet of said ultrasonic generator to convert the electric oscillations or signals into ultrasonic mechanical vibrations, a hollow needle with an axially disposed bore, having one end thereof connected to said magnetostriction converter to receive the mechanical vibrations causing tissue to be fragmented and the severed tissue to be aspirated, while its other free end is adapted to be brought into contact with the tissue to be removed. According to the invention, said free end is provided with an end wall portion having a through opening communicating with the needle axial bore and having a diameter substantially less than the diameter of the axial bore.

An advantage of a device of the character described resides in the fact, proven by experience, that its use yields a totally unexpected effect consisting in significant spontaneous aspiration of broken and emulsified ocular tissues, whereby the special suction unit is rendered superfluous.

Although the inventors do not desire to commit themselves by any definitive theoretical statements, it is their belief that such an unexpected effect accrues from a very low pressure which develops at the point of direct contact between the opening in the end wall portion and the axial bore of the needle on the one hand, and the broken tissue on the other.

It is preferred for the diameters of the axial bore and the opening in the end wall portion to be in the ratio of from about ⅓ to about ⅔ since at this quantitative relation aspiration of the emulsified mass is most effective.

Further increase of suction and fragmentation efficacy with respect to ocular tissues is secured by the use of a tapered needle whose outer surface is bevelled from the junction of the needle with a source of ultrasonic vibrations in the form of a converter to the end wall portion.

Enhanced efficiency of fragmentation and aspiration of intraocular tissues is apparently due to the fact that the needle form of the invention is gradually thinning out, serves, as it were, as an extension of a concentrator inserted in between the magnetostriction converter and the needle, which is conductive to better transmission of longitudinal ultrasonic vibrations from the converter to the needle and, therefore, to its distal end, whereby the power of its vibrations is amplified.

An even further enhancement of fragmenting efficiency obtained with the apparatus of this invention is achieved owing to the sharp cutting edge provided circumferentially continuously along the end wall portion.

The sharp cutting edge of the end wall portion, in addition to the fragmenting action on interocular tissues of a purely mechanical nature, has the properties of an ultrasound focusing element at the same time augmenting the effect of cavitation viewed as a material constituent within the mechanism of ultrasonic fragmentation.

However, it should be repeatedly underscored that the speculations put forward hereinbefore lay no claims to being exhaustive and should in no wise be regarded as limiting the scope of the present invention, all the more so, since this invention has resulted in a totally unexpected effect.

BRIEF DESCRIPTION OF THE DRAWINGS

The present invention will be further described, by way of example only, with reference to the accompanying drawings, wherein.

DESCRIPTION OF THE PREFERRED EMBODIMENTS

Figure 1:
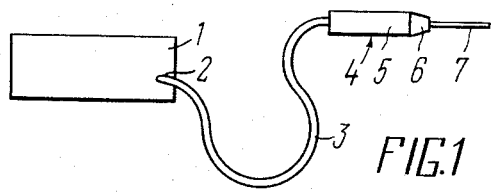
FIG. 1 is a block diagram of the apparatus for the fragmentation and aspiration of cataract.
Figure 2:
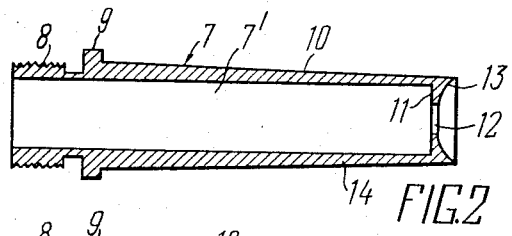
FIG. 2 is a cross-sectional view showing the needle of the apparatus for the fragmentation and aspiration of cataract, according to the invention, having a bevelled outer surface and a sharp cutting edge on the end wall portion.

Referring to FIG. 1, there is shown an apparatus for the fragmentation and aspiration of cataract in its entirety. The apparatus comprises an ultrasonic generator 1, which is essentially any ultrasonic generator, capable of providing an output frequency of vibrations of from 20 to 70 KHz, for example, as disclosed in U.S. Pat. No. 3,589,363. An output 2 of the generator is connected with the help of a cable to a surgical handpiece 4, which directly performs the fragmentation and aspiration of cataract. The handpiece 4 consists of a magnetostriction converter 5 similar to the devices disclosed in U.S. Pat. Nos. 3,589,363 and 3,990,452. Furthermore, this unit comprises a concentrator of ultrasonic vibrations 6, also referred to in the above-mentioned U.S. Patents. A needle 7 (FIG. 2) is provided with a threaded shank 8 to enable its connection to concentrator 6, and a flat 9 for tightening of this connection with a wrench. A housing 10 of the needle 7 is made hollow forming an axial bore 7' therein. The housing 10 is provided with an end wall portion 11 arranged substantially at right angles to the axis of the bore 7'. An axial opening 12 is made through the wall 11 to communicate with the bore 7'. It has been found that the diameter of the opening 12 must be in the range of between ⅓ and ⅔ of the diameter of the bore 7'. An outer edge 13 of the end wall portion is made sharp. An outer surface 14 of the housing 10 is provided with a conical bevel extending from the junction of the needle with the converter 5, thereby permitting higher concentration of the ultrasonic vibrations.

Figure 5:
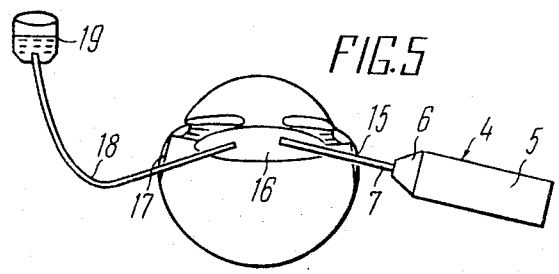
FIG. 5 is a section of the surgical space showing the arrangement of parts of the apparatus in operative position.

The apparatus is operated as follows. The needle 7 is introduced into the eye through an incision 15 in its wall, (FIG. 5) then advanced to the area of intraocular tissue to be broken apart and removed, such as lens 16. On activation of the ultrasonic generator, the electric oscillations are transformed into mechanical vibrations in the converter 5, which are subsequently transmitted to the needle 7. The ultrasonic vibrations emitted by the needle 7 cause the tissue of the lens 16 adjacent the free end of said needle to be broken apart. The fragmented mass of intraocular tissue is sucked up due to a negative or lowered pressure produced during vibrations of the needle having the end wall portion provided with the opening. Following fragmentation and aspiration of the intraocular tissue subject to surgical removal, the needle is withdrawn from the eye and the incision on its wall closed. Depletion or loss of intraocular matter by volume resulting from surgery is offset by infusion of the saline solution or a substituting fluid through a separate incision 17 made in the wall of the eye either contemporaneously with aspiration or on completion of removal using a special instrument 18 from a reservoir 19.

The apparatus of this invention was surgically tested in 278 patients, 155 of which number were operated for cataract, while the remaining 123 for pathology of the vitreous.

Among the cataract patients 104 individuals presented with presenile and complicated cataracts, the age brackets being 35 and 55 years, density of the nucleus was plus 2 and plus 3, in 31 patients a post-traumatic cataract was removed within a period of from 10 hours to 14 days following the injury against a background of traumatic iridocyclitis. 20 children suffering from congenital cataracts aged 2-3 months also underwent surgery.

Among the subjects with pathology of the vitreous 49 showed opacification of the vitreous of a post-traumatic etiology, 46 individuals exhibited aphakix vitreous block, 23—opacification of the vitreous of a diabetic and inflammatory genesis, 5 patients were with endophthalmitis.

All patients showed a good anatomical response, and the functional improvement was evaluated in each case by the condition of the cornea, retina, and optical nerve.

What follows is a series of concrete examples of using the apparatus of this invention.

Female patient N., 52 years old, on admission diagnosed complicated cataract in the right eye. The eye was quiet, the cornea and the anterior chamber fluid were transparent. Contours of the iris well defined, the pupil round, 4 mm in diameter, with a vivid reaction to light. Angle of the anterior chamber open, of moderate width, faint pigmentation present in the area of Schlemm's canal and corneoscleral trabeculae.

Opacity of the lens engulfed the entire mass of the lenticular matter. Visual acuity in the operated eye was 0.03. Visual field was in norm.

The intraocular pressure as registered by daily tonometry varied between 17.0 and 24.0 mm Hg.

The vitreous showed no pathological changes.

The patient underwent surgery ultrasonic phacofragmentation under local anesthesia performed through pars plana of the ciliary body using the apparatus of this invention. The instrument was operated at a frequency of 66 KHz. for 2 minutes. A balanced salt solution was utilized as the substitutive fluid. Surgery was uneventful with individually performed removal of the broken lenticular matter.

In the first 1-2 day period following surgery there was mild hyperemia and swelling of the conjunctiva of the eyeball around the operative incisions. The pupillary space was free from the cortical mass.

The patient received instillations of mydriatics, hydrocortisone, and sodium sulpacyle. On the third day after surgery in view of the abatement of inflammatory signs the patient was discharged from hospital. Visual acuity with aphakic correction at discharge was $-1.0$. At the time of a followup examination carried out 3 months following the operated eye was quiet, the cornea was clear and had a glossy appearance. The anterior chamber was deep and filled with clear fluid. The iris was quiet with well-defined borders giving evidence of marked iridodesis. The pupil retained a round shape and vivid reaction to light, having a diameter of 3 mm. Angle of the anterior chamber was open and very with some buildup of the exogenous pigmentation in the area of Schlemm's canal and the corneoscleral trabecula as compared to its pre-operative appearance. The central part of the pupil was clear, however, shreds of the capsular material were noted on dilating the pupil along the periphery. Fundal reflex was clear-cut, no pathological changes of the funds were detected opthalmoscopically.

Visual acuity with spheric correction was $-1.0$. The patient showed a normal visual field. The intraocular pressure as provided by the daily tonometric readings varied in the range of 16.0 to 23.0 mm Hg. Echographically, there were no detectable pathological changes either in the vitreous or in the retina.

Patient B., 20 years old, prior to admission documented post-traumatic cataract, opacification of the vitreous in the left eye.

Duration of cataract history documented in the patient's record was 3 years. Visual acuity in the left eye was 0.01. On examination of the visual field no pathological changes were detected. Biomicroscopically there was some evidence of stromal atrophy affecting the iris and pupilary border. There was formation of posterior synechiae, pigmental deposits on the anterior capsule of the lens.

Lenticular transparency partially persisted in the periphery. Gonioscopic evaluation revealed a medium width of the angle of the anterior chamber. Pigmentation of the angular zones was for the most part moderate with cone-like goniosynechiae. Echographic examination exposed destructive changes of the vitreous. The intraocular pressure as given by daily tonometry was within 22.0 and 26.0 mm Hg.

The patient underwent surgical removal of the cataract and opacity of the vitreous using the apparatus of this invention as hereinbefore described.

The cataract was removed through a scleral incision 1.5 mm long made 4 mm away from the limbus in the pars plana of the ciliary body at 2 o'clock.

Another perforating incision of the sclera also 4 mm away from the limbus at 10 o'clock provided an entrance through which along the equator of the lens a needle introducing a balanced salt solution was inserted. Mydriasis of the pupil was accomplished by introducing into the posterior chamber through the scleral incision of a 1% mesatone solution. Operation of the instrument continued for 1.5 minutes.

Aspiration of the broken lenticular and vitreous masses was performed independently without a special suction device. The emulsion suction rate was controlled by changing the power of the transmitted ultrasonic signal. Post-operative period was uneventful.

During the first days following surgery there was a mild swelling and hyperemia of the conjunctiva, and a mild evidence of iritis.

By the end of the seventh day the inflammation appeared to have resolved and the patient was discharged from the hospital. At discharge the cornea and fluid in the anterior chamber were clear, the anterior chamber was deep with the pupil retaining the round shape.

Visual acuity with correction showed by the patient at discharge was 0.8.

At the time of repeated examination the eyeball was quiet, the cornea clear, fluid in the anterior chamber transparent. The structure of the anterior chamber was deep, even, with signs of iridodonesis.

The pupil remained round in form. The pupillary area was clear.

Gonioscopically the angle of the anterior chamber was shown to be open. Exogenous pigmentation of the angular zones was moderately developed.

There were no opthalmoscop confirmed pathological changes in the fundus. The intraocular pressure determined by daily tomography fell in the range of 16.0 to 21.0 mm Hg.

Visual acuity with correction was plus 10.0 D. was 1.0.

Figure 3:
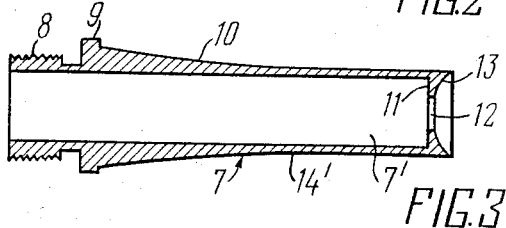
FIG. 3 is a cross-sectional view of a needle substantially identical with the needle in FIG. 2, but provided with a parabolically shaped outer surface.
Figure 4:
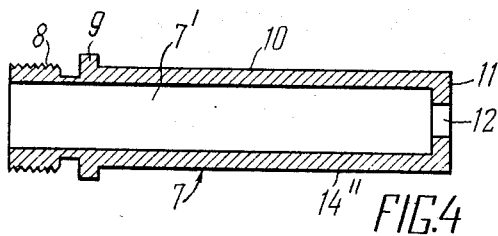
FIG. 4 is a cross-sectional view of the needle having a cylindrical shape.

Though the example rendered hereinbefore constitutes the preferred usage, alternative applications are possible, for example, such as shown in FIGS. 3 and 4. Thus, the device shown in FIG. 3 is substantially similar to that shown in FIG. 2 and disclosed above, the only difference being that the surface 14' is made parabolic, while the instrument depicted in FIG. 4 differs only in that the surface 14' is made cylindrical having no sharp parts. The alternative versions of the apparatus illustrated in FIGS. 3 and 4 are subject to the operation procedure as disclosed in the foregoing description.

While we have described our invention with respect to the details of a preferred and alternative embodiments thereof, many changes in construction, dimensions and relative configuration of constituent parts, as well as operational sequence will suggest themselves to those skilled in the art to which this invention relates without departing from the meaning and range of the appended claims.

What is claimed is:

1. In a ultrasonic device adapted to fragment and aspirate ocular tissue comprising a controlled ultrasonic generator connected to a magnetostriction converter to convert electric vibrations into ultrasonic mechanical vibrations, and a hollow needle with an axially disposed bore having one end thereof connected to said magnetostriction converter to receive the mechanical vibrations to cause ocular tissues to be fragmented and to sever tissue that is to be aspirated, the other free end of said needle being adapted to be brought into contact with tissue that is to be removed, the improvement residing in that the end of said needle adapted for interaction with the tissue to be removed is provided with a transverse end wall portion means having a through opening with a diameter substantially less than the diameter of the axial bore of the needle, said opening and said bore being joined together at said end wall portion means to create a vacuum to aspirate the ocular tissue.

2. Apparatus of claim 1, wherein the diameter of the opening of the end wall portion is substantially between $\frac{1}{3}$ and $\frac{2}{3}$ of the diameter of said needle bore.

3. Apparatus of claim 1, wherein an outer surface of said needle is bevelled from the junction of said needle with said converter of ultrasonic vibrations to the end wall portion.

4. Apparatus of claim 1, wherein a projecting end of said end wall portion has a sharp cutting edge.

5. Apparatus of claim 4, wherein said sharp cutting edge extends continuously over the periphery of said wall portion.

* * * * *